(12) United States Patent  
Crandall

(10) Patent No.: US 8,172,242 B1
(45) Date of Patent: May 8, 2012

(54) MEDICAL IMAGING WORKSTATION

(76) Inventor: Thomas Crandall, Medford, OR (US)

( * ) Notice: Subject to any disclaimer, the term of this patent is extended or adjusted under 35 U.S.C. 154(b) by 673 days.

(21) Appl. No.: 12/380,518

(22) Filed: Feb. 27, 2009

Related U.S. Application Data

(60) Provisional application No. 61/068,409, filed on Mar. 6, 2008.

(51) Int. Cl.
A61B 6/00 (2006.01)
(52) U.S. Cl. .................. 280/47.35; 378/197; 378/198
(58) Field of Classification Search .......... 378/195–198; 280/47.11, 47.18, 47.19, 47.35
See application file for complete search history.

(56) References Cited

U.S. PATENT DOCUMENTS

| 3,801,790 | A | 4/1974 | Gotzl et al. |
| 5,206,894 | A | 4/1993 | Makrinos et al. |
| 5,425,069 | A | 6/1995 | Pellegrino et al. |
| 5,475,730 | A * | 12/1995 | Galando ................ 378/157 |
| 6,007,243 | A | 12/1999 | Ergun et al. |
| 6,131,680 | A * | 10/2000 | Nii et al. ............ 180/65.235 |
| 6,193,415 | B1 | 2/2001 | Kadowaki et al. |
| 6,237,707 | B1 | 5/2001 | Lyke et al. |
| 6,851,853 | B2 | 2/2005 | Nakagawa et al. |
| 7,016,467 | B2 | 3/2006 | Brooks |
| 7,438,470 | B2 | 10/2008 | Koren |
| 7,798,710 | B1 * | 9/2010 | Barnes et al. ............ 378/206 |
| 2006/0034427 | A1 * | 2/2006 | Brooks ................ 378/198 |
| 2008/0240535 | A1 * | 10/2008 | Frangioni et al. ........ 382/131 |

* cited by examiner

Primary Examiner — J. Allen Shriver, II
Assistant Examiner — James Triggs
(74) Attorney, Agent, or Firm — Jerry Haynes Law

(57) ABSTRACT

A workstation includes a cart, a generally elongated linear actuator carried by the cart, a support arm assembly comprising a rail support arm adjustably carried by the linear actuator, a camera support rail adjustably carried by the rail support arm along an axis generally perpendicular to a longitudinal axis of the linear actuator and an arm motor engaging the rail support arm. The rail support arm traverses the linear actuator responsive to operation of the arm motor.

10 Claims, 6 Drawing Sheets

MEDICAL IMAGING WORKSTATION

CROSS-REFERENCE TO RELATED APPLICATIONS

This application claims the benefit of and incorporates by reference in its entirety U.S. provisional patent application No. 61/068,409, filed Mar. 6, 2008 and entitled "IR Medical Thermal Imaging Workstation".

FIELD OF THE INVENTION

The present disclosure relates to medical infrared imaging systems. More particularly, the present disclosure relates to a medical infrared imaging workstation which is suitable for supporting a medical infrared imaging workstation in a portable and positionally versatile manner.

BACKGROUND OF THE INVENTION

State-of-the-art medical infrared imaging systems are known which use infrared cameras to generate digital infrared images for the early detection of breast cancer and other health-related conditions. Digital infrared imaging has proven to be of great value in aiding with the detection and analysis of inflammatory and circulatory conditions and other health-related conditions which may not be detected using conventional medical, imaging processes. The digital infrared imaging procedure is painless, does not contact the patient's body and does not use ionizing radiation. Digital infrared images may be used as an adjunctive tool alongside other forms of imaging and examination procedures when used in the early detection of breast cancer and other health-related conditions.

Digital infrared imaging systems which are currently in use may utilize state-of-the-art, un-cooled shielded focal plane array detectors that are virtually maintenance-free. The system may be used in a controlled environment and may not have portability as a primary feature as do most currently-available medical infrared cameras.

A medical imaging workstation is therefore needed which is suitable for supporting a medical imaging workstation in a portable and positionally versatile manner and which may be used to facilitate remote focus, automatic camera lift and horizontal camera adjustments of an infrared camera.

SUMMARY

The present disclosure is generally directed to a workstation. An illustrative embodiment of the workstation includes a cart, a generally elongated linear actuator carried by the cart, a support arm assembly comprising a rail support arm adjustably carried by the linear actuator, a camera support rail adjustably carried by the rail support arm along an axis generally perpendicular to a longitudinal axis of the linear actuator and an arm motor engaging the rail support arm. The rail support arm traverses the linear actuator responsive to operation of the arm motor.

BRIEF DESCRIPTION OF THE DRAWINGS

The disclosure will now be made, by way of example, with reference to the accompanying drawings, in which.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description.

Figure 3:
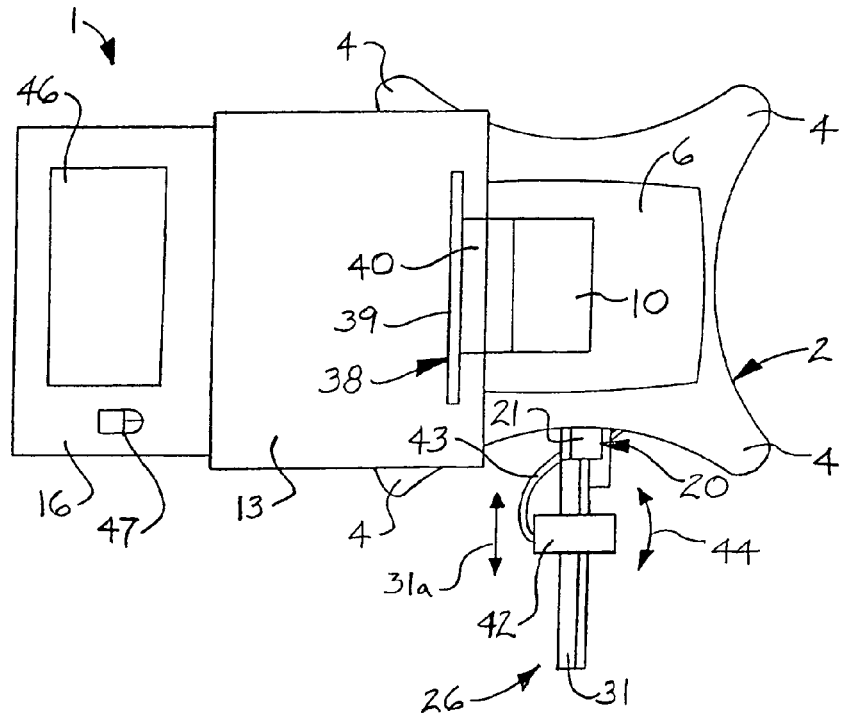
FIG. 3 is a top view of an illustrative embodiment of the medical imaging workstation, more particularly illustrating multi-positioning capability of an infrared camera provided on the medical imaging workstation.
Figure 4:
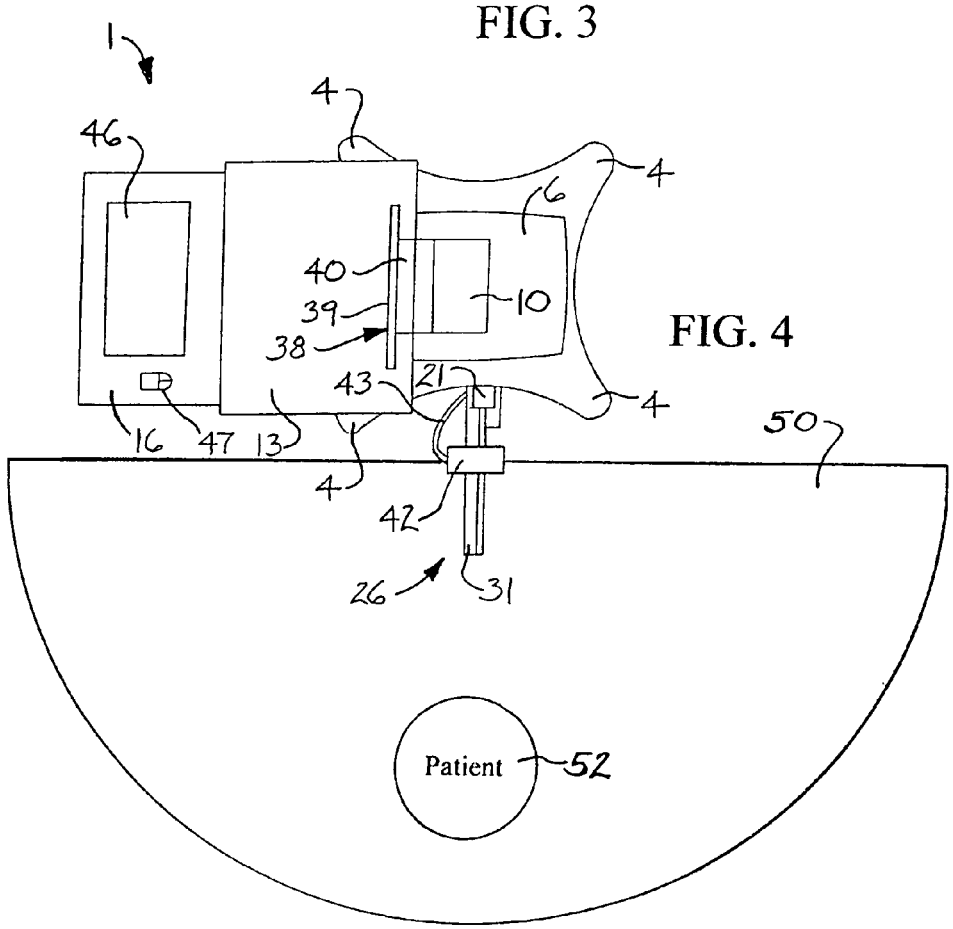
FIG. 4 is a top view of an illustrative embodiment of the medical imaging workstation, more particularly illustrating imaging of a patient in implementation of an illustrative embodiment of the medical imaging workstation.
Figure 5:
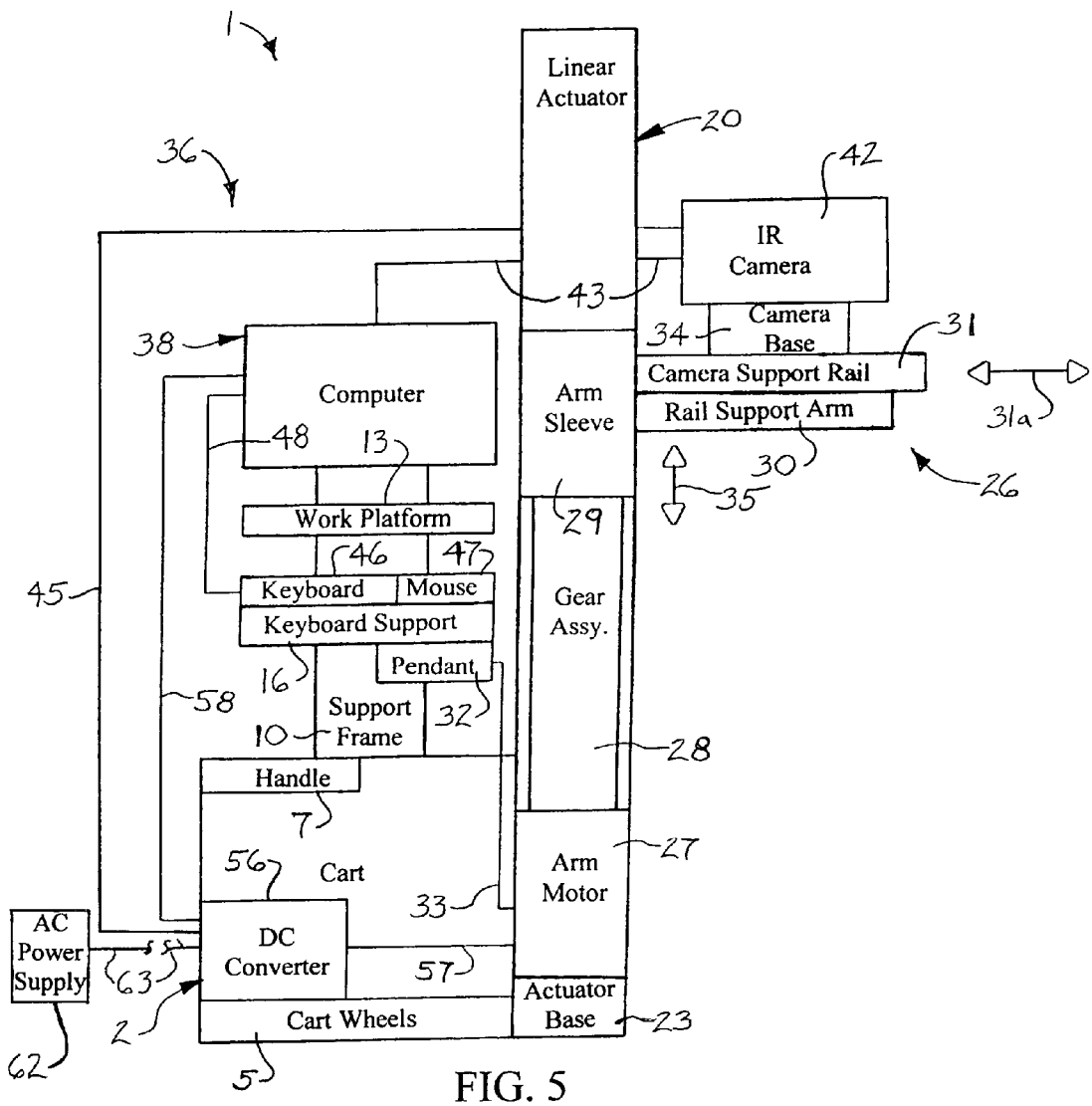
FIG. 5 is a functional block diagram of an illustrative embodiment of the medical imaging workstation.

Referring initially to FIGS. 1-6 of the drawings, an illustrative embodiment of the medical imaging workstation is generally indicated by reference numeral 1. The medical imaging workstation 1 includes a medical-grade cart 2 which may have a cart frame 3. Multiple cart legs 4 may extend outwardly from the cart frame 3. Cart wheels 5, each of which may be a castor-type wheel, for example and without limitation, may be provided on the respective cart legs 4. A cart body 6 may be provided on the cart frame 3. As illustrated in FIG. 5, in some embodiments a cart handle 7 may be provided on the cart body 6 or elsewhere on the cart 2 to facilitate pushing and/or pulling of the cart 2 across a floor or other surface (not illustrated) on the cart wheels 5.

As illustrated in FIG. 5, in some embodiments a DC converter 56 may be provided in the cart 2. A power cord 63, which may be adapted to plug into an AC power supply 62 such as a standard 120-volt household electrical outlet, for example and without limitation, may be connected to the DC converter 56 and extend from the cart 2.

Figure 2:
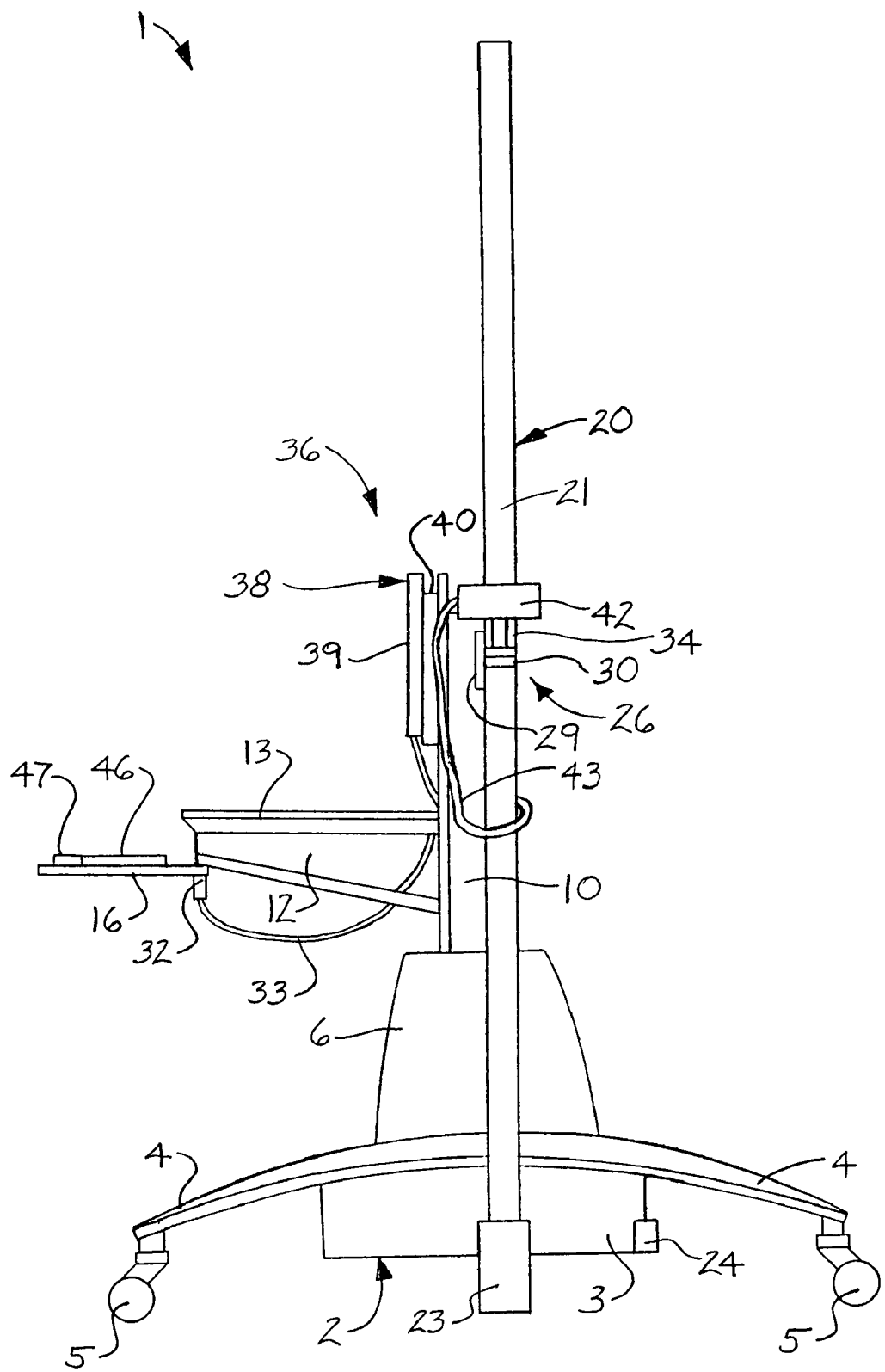
FIG. 2 is a side view of an illustrative embodiment of the medical imaging workstation.

A vertical support frame 10 may extend upwardly from the cart body 6 of the cart 2. In some embodiments, a work platform 13 may be mounted on the support frame 10, such as via a platform support bracket 12 of suitable design. A keyboard support platform 16 may additionally be mounted on the support frame 10. As illustrated in FIG. 2, in some embodiments the keyboard support platform 16 may extend from the platform support bracket 12. The work platform 13 and/or the keyboard support platform 16 may be vertically adjustable on the support frame 10 according to the knowledge of those skilled in the art. For example, vertical adjustability of the work platform 13 and/or the keyboard support platform 16 on the support frame 10 may enable sitting or standing of an operator (not illustrated) at the medical imaging workstation 1.

Figure 1:
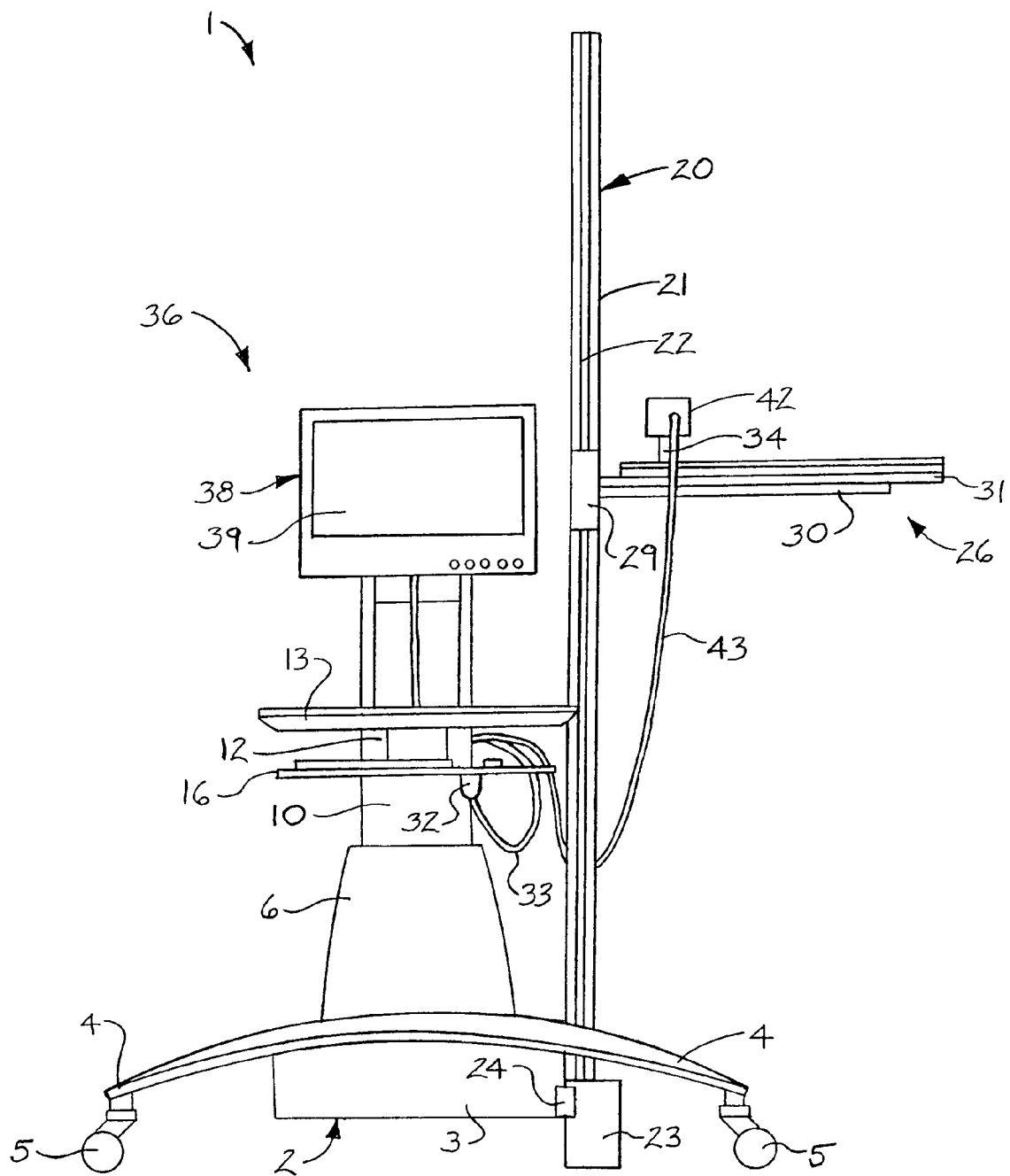
FIG. 1 is a front view of an illustrative embodiment of the medical imaging workstation.

A linear actuator 20 may extend upwardly from the cart 2. The linear actuator 20 may include an actuator base 23 which may be attached to a side of the cart frame 3 according to the knowledge of those skilled in the art. In some embodiments, the actuator base 23 may be detachably attached to the cart frame 3 of the cart 2 via an actuator attachment bracket 24. A generally elongated actuator housing 21 extends upwardly from the actuator base 23. As illustrated in FIG. 1, an elongated actuator housing slot 22 may be provided in the actuator housing 21 and may traverse substantially the entire length of the actuator housing 21 for purposes which will be hereinafter described.

A support arm assembly 26 may be provided on the linear actuator 20. As illustrated in FIG. 5, the support arm assembly 26 may include an arm motor 27 which may be provided in the actuator housing 21. The arm motor 27 may be electrically connected to the DC converter 56 through a motor cable 57. An arm sleeve 29 may be slidably mounted and vertically adjustable on the actuator housing 21, as indicated by the arrow 35 in FIG. 5. A gear assembly 28 in the actuator housing 21 may be drivingly engaged by the arm motor 27 and drivingly engage the arm sleeve 29 through the actuator housing slot 22 (FIG. 1). The gear assembly 28 may be any mechanism which is known by those skilled in the art that is capable of translating rotational motion of the arm motor 27 into vertical motion of the arm sleeve 29 on the actuator housing 21. In various embodiments the gear assembly 28 may be a lead screw, a ball screw or a belt drive, for example and without limitation. As further illustrated in FIG. 5, in some embodiments a motor control pendant 32 may be connected to the arm motor 27 through a pendant cable 33 for user control of the arm motor 27 and selected upward and downward travel of the arm sleeve 29 on the linear actuator 20.

The support arm assembly 26 may further include a generally elongated rail support arm 30 which extends outwardly from the arm sleeve 29. The rail support arm 30 may be oriented in generally perpendicular relationship with respect to the longitudinal axis of the linear actuator 20. A camera support rail 31 may be slidably mounted on the rail support arm 30. The camera support rail 31 may be capable of sliding back and forth on the rail support arm 30 as indicated by the arrow 31a. In some embodiments, a camera base 34 may be provided on the camera support rail 31 to support an infrared camera 42 of a medical imaging system 36, in typical application of the medical imaging workstation 1 which will be hereinafter described. As shown in FIG. 3, the infrared camera 42 may be capable of pivoting with respect to the camera support rail 31 as indicated by the arrow 44.

In some applications, the medical imaging workstation 1 may be used to support a medical imaging system 36. The medical imaging system 36 may include a computer 38 having a computer monitor 39 (FIGS. 1-4) which may be provided on the support frame 10. In some embodiments, the computer 38 may be attached to the support frame 10 using a computer mount bracket 40 (FIGS. 2 and 3). The computer mount bracket 40 may be vertically adjustable on the support frame 10 according to the knowledge of those skilled in the art. The computer 38 may be electrically connected to the DC converter 56 through a computer cable 58. A keyboard 46 and a mouse 47 may be provided on the keyboard support platform 46 and connected to the computer 38 through a keyboard/mouse cable 48.

A digital medical infrared camera 42 may be provided on the camera base 34 on the camera support rail 31. The infrared camera 42 may be connected to the computer 38 through a video cable 43 and may be electrically connected to the DC converter 56 through a camera cable 45. The infrared camera 42 may be capable of being manually pivoted on the camera base 34 to a selected angle with respect to the camera support rail 31, as indicated by the arrow 44 in FIG. 3. Moreover, the lateral position of the infrared camera 42 with respect to the linear actuator 20 may be manually adjusted as indicated by the arrow 31a by sliding the camera support rail 31 outwardly from the linear actuator 20 on the rail support arm 30.

Referring to FIG. 4, in typical application of the medical imaging workstation 1, the cart 2 is transported to a desired location in a clinic, medical office, hospital or other medical facility. The cart 2 may be transported across a floor (not illustrated) or other supporting surface by grasping the cart handle 7 (FIG. 5) and rolling the cart wheels 5 on the floor or surface. When the cart 2 is positioned at the desired location, the power cord 63 may be plugged into the AC power supply 62. The DC converter 56 converts AC electrical power which is supplied by the AC power supply 62 into DC power that is supplied to the computer 38 and the arm motor 27 of the linear actuator 20. The height of the work platform 13 and the keyboard support platform 16 may be adjusted on the support frame 10 as needed according to the preferences of the user.

As illustrated in FIG. 4, a patient 52 is positioned at a location generally in front of the IR camera 42. The patient 52 may be sitting, standing or reposed in some other position. The lateral position of the IR camera 42 may be adjusted along the rail support arm 30, as indicated by the arrow 31a (FIG. 5), and the angular position of the IR camera 42 relative to the rail support arm 30 may be adjusted as indicated by the arrow 44 (FIG. 3), to locate the patient 52 within the optical field 50 of the IR camera 42. Items (not illustrated) such as the patient's file, for example, may be placed on the work platform 13. Accordingly, digital infrared images of the patient 52 can be captured by the IR camera 42 and transferred to the computer 38. The digital infrared images of the patient 52 can be displayed on the monitor 39 of the computer 38 and saved on the computer 38 typically for diagnostic purposes. It will be appreciated by those skilled in the art that the vertical adjustment capability of the arm sleeve 29 on the linear actuator 20 and the lateral adjustment capability of the IR camera 42 on the camera support rail 31 enables an imaging technician (not illustrated) to precisely adjust the vertical and horizontal positions of the IR camera 42 without having to move the patient 52.

Figure 6:
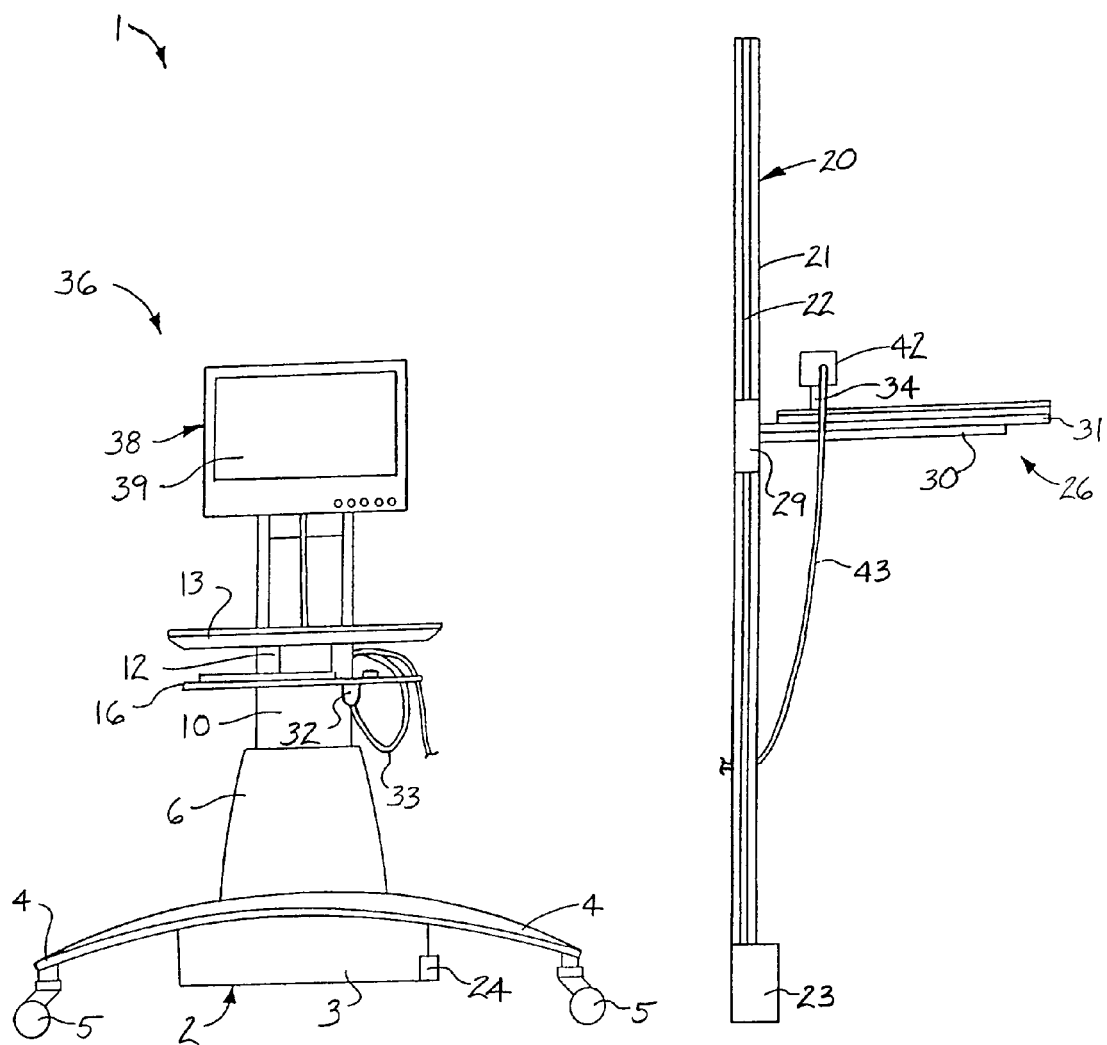
FIG. 6 is a front view of an illustrative embodiment of the medical imaging workstation, with the linear actuator detached from the cart of the workstation.

As illustrated in FIG. 6, in some embodiments of the medical imaging workstation 1, the linear actuator 20 can be detached from the cart 2 and disposed in a free-standing position at a selected distance from the cart 2. The linear actuator 20 may support the IR camera 42 in the desired proximity to the cart 2, with the video cable 43 connecting the IR camera 42 to the computer 38 and the motor cable 57 connecting the arm motor 27 to the DC converter 56 on the cart 2.

Figure 7:
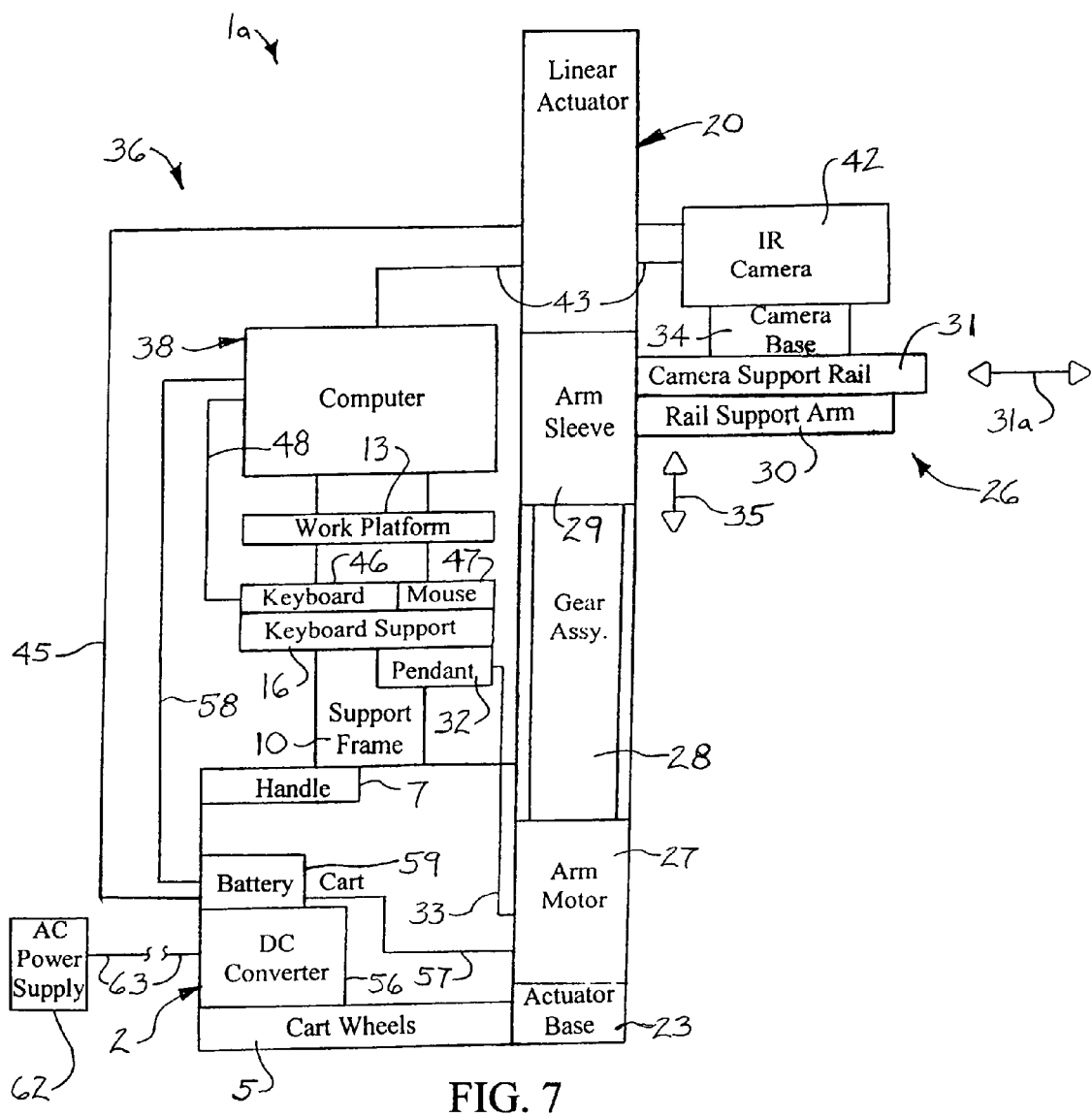
FIG. 7 is a functional block diagram of an alternative illustrative embodiment of the medical imaging workstation.

Referring next to FIG. 7 of the drawings, an alternative illustrative embodiment of the medical imaging workstation 1a includes a battery 59 which may be electrically connected to the DC converter 56. The arm motor 27 of the support arm assembly 26 may be electrically connected to the battery 59 via the motor cable 57. The computer 38 may be electrically connected to the battery 59 via the computer cable 58. The IR camera 42 may be electrically connected to the battery 42 via the camera cable 45. In some embodiments, the battery 59 may be rechargeable via the AC power supply 62 and the power cord 63. In application of the medical imaging workstation 1a, the battery 59 provides portable electrical power to the arm motor 27, the computer 38 and the IR camera 42. This expedient facilitates use of the medical imaging workstation 1 at a location which is remote from the AC power supply 62.

While the illustrative embodiments of the disclosure have been described above, it will be recognized and understood that various modifications can be made in the disclosure and the appended claims are intended to cover all such modifications which may fall within the spirit and scope of the disclosure.

I claim:

1. A workstation, comprising:
a cart having a plurality of cart wheels;
a support frame carried by the cart;
at least one platform carried by the support frame;
a linear actuator having an actuator base carried by the cart, a generally elongated actuator housing carried by the actuator base and an actuator housing slot provided in the actuator housing; and
a support arm assembly comprising an arm sleeve adjustably carried by the actuator housing of the linear actuator, a rail support arm carried by arm sleeve, a camera support rail adjustably carried by the rail support arm along an axis generally perpendicular to a longitudinal axis of the actuator housing, an arm motor provided in the actuator housing and a gear assembly drivingly engaged by the arm motor and drivingly engaging the arm sleeve through the actuator housing slot.

2. The workstation of claim 1 wherein the at least one platform comprises a work platform and a keyboard support platform.

3. The workstation of claim 2 wherein the work platform and the keyboard support platform are adjustable on the support frame.

4. The workstation of claim 1 further comprising a motor control pendant connected to the arm motor.

5. The workstation of claim 1 further comprising an actuator attachment bracket detachably attaching the actuator base of the linear actuator to the cart.

6. The workstation of claim 1 further comprising a DC converter provided in the cart and electrically connected to the arm motor and a power cord electrically connected to the DC converter.

7. The workstation of claim 6 further comprising a rechargeable battery electrically connected to the DC converter and wherein the arm motor is electrically connected to the rechargeable battery.

8. The workstation of claim 1 wherein the base comprises a cart frame, a plurality of cart legs carried by the cart frame and a cart body carried by the cart frame and wherein the plurality of cart wheels is carried by the plurality of cart legs, respectively, and the support frame is carried by the cart body.

9. A workstation, comprising:
a cart having a plurality of wheels;
a support frame carried by the cart;
a computer having a computer monitor carried by the support frame;
at least one platform carried by the support frame;
a gear assembly drivingly engaged by the arm motor and drivingly engaging the rail support arm;
a generally elongated linear actuator carried by the cart, wherein the linear actuator comprises an actuator base carried by the cart, a generally elongated actuator housing carried by the actuator base and an actuator housing slot provided in the actuator housing, and wherein the gear assembly engages the rail support arm through the actuator housing slot;
a support arm assembly comprising a rail support arm adjustably carried by the linear actuator, a camera support rail adjustably carried by the rail support arm along an axis generally perpendicular to a longitudinal axis of the linear actuator, a camera base carried by the camera support rail and an arm motor engaging the rail support arm;
wherein the rail support arm traverses the linear actuator responsive to operation of the arm motor; and
an infrared camera carried by the camera base and connected to the computer.

10. The workstation of claim 9 further comprising a motor control pendant connected to the arm motor.

* * * * *